US012734136B2

(12) United States Patent
Holm et al.

(10) Patent No.: US 12,734,136 B2
(45) Date of Patent: Sep. 15, 2026

(54) INTRANASAL ADMINISTRATION OF KETAMINE TO CLUSTER HEADACHE PATIENTS

(71) Applicant: Afyx Development A/S, Hørsholm (DK)

(72) Inventors: Per Holm, Vanløse (DK); Ole Pedersen, Smørum (DK); John Claude Krusz, Dallas, TX (US)

(73) Assignee: Afyx Development A/S, Hørsholm (DK)

( * ) Notice: Subject to any disclaimer, the term of this patent is extended or adjusted under 35 U.S.C. 154(b) by 587 days.

(21) Appl. No.: 17/595,766

(22) PCT Filed: May 29, 2020

(86) PCT No.: PCT/IB2020/000432

§ 371 (c)(1),
(2) Date: Nov. 23, 2021

(87) PCT Pub. No.: WO2020/240279

PCT Pub. Date: Dec. 3, 2020

(65) Prior Publication Data

US 2022/0218627 A1 Jul. 14, 2022

Related U.S. Application Data

(60) Provisional application No. 62/855,543, filed on May 31, 2019.

(51) Int. Cl.
*A61K 31/135* (2006.01)
*A61K 9/00* (2006.01)
*A61K 9/08* (2006.01)
*A61P 29/00* (2006.01)

(52) U.S. Cl.
CPC .......... *A61K 31/135* (2013.01); *A61K 9/0043* (2013.01); *A61K 9/08* (2013.01); *A61P 29/00* (2018.01)

(58) Field of Classification Search
CPC .................................................... A61K 31/135
See application file for complete search history.

(56) References Cited

U.S. PATENT DOCUMENTS 6,248,789 B1 * 6/2001 Weg ..................... A61K 31/135 424/435
2014/0057988 A1 * 2/2014 Weg ....................... A61K 9/006 514/647
2014/0275278 A1 9/2014 Basstanie et al.
2018/0177743 A1 * 6/2018 Jay ......................... A61K 47/36
2018/0177744 A1 6/2018 Jay

FOREIGN PATENT DOCUMENTS

WO WO-2019126108 A1 * 6/2019 ........... A61K 31/135

OTHER PUBLICATIONS

Singh et al. (Pharmacotherapy, 38 (3):390-401, 2018).*
Bergman, Stewart A. "Ketamine: Review of Its Pharmacology and Its Use in Pediatric Anesthesia" Anesth Prog, 1999, pp. 10-20, vol. 46.
Ekbom, K. et al., "Age at onset and sex ratio in cluster headache: observations over three decades" Cephalalgia, 2002, pp. 94-100, vol. 22.
Fischera, M. et al., "The incidence and prevalence of cluster headache: a meta-analysis of population-based studies" Cephalalgia, 2008, pp. 614-618, vol. 28.
Gaul, Charly et al., "Treatment costs and indirect costs of cluster headache: A health economics analysis" Cephalalgia, 2011, pp. 1664-1672, vol. 31, No. 16.
Granata, L. et al., "Ketamin i. v. zur Behandlung von Clusterkopfschmerz" Schmerz, 2016, pp. 286-288, vol. 30.
Jensen, RM et al., "Burden of cluster headache" Cephalalgia, 2007, pp. 535-541, vol. 27.
Krusz, John Claude "P02.168—IV Ketamine in the Clink To Treat Cluster Headache" Neurology, Mar. 2009, pp. A89-A90, vol. 72, Suppl. 3.
Krusz, J. et al., "(268) IV ketamine treatment for multiple headache and pain disorders" 2009, S43.
Krusz, JC et al., "IV Ketamine: Rapid Treatment for All TAC Subtypes in the Clinic" Jun. 2011, Abstract Poster #72, 15th Congress of the International Headache Society, Berlin Germany, Poster 2- 110.
Krusz, J.C. "P10 IM Ketamine: Rapidly Treating Various Migraine and Headaches in the Clinic" 54$^{th}$ Annual Scientific Meeting American Headache Society, Jun. 2012, Program Abstracts.
Krusz, John Claude "Intranasal Ketamine for the Relief of Cluster Headache" 17 Articles in vol. 19, Issue #4, pp. 36-37, Jun. 2019.
Lapidus, Kyle A.B. et al., "A Randomized Controlled Trial of Intranasal Ketamine in Major Depressive Disorder" Biol Psychiatry, Dec. 2014, pp. 970-976, vol. 76, No. 12.
Lund, Nunu et al., "Chronobiology differs between men and women with cluster headache, clinical phenotype does not" Neurology, Mar. 2017, pp. 1069-1076, vol. 88.
Matharu, Manjit "Cluster Headache" Clinical Evidence, 2010, pp. 1-39, vol. 2, No. 1212.

(Continued)

*Primary Examiner* — Bong-Sook Baek
(74) *Attorney, Agent, or Firm* — Adams & Reese LLP

(57) ABSTRACT

Provided is a method of treating patients with Cluster Headache (CH) including chronic Cluster Headache (cCH) comprising intranasal administration to a patient in need thereof of an aqueous composition, e.g., pharmaceutical composition, comprising a therapeutically effective amount of ketamine, which may reduce or eliminate side effects of ketamine when used in the treatment of Cluster Headache, and to a composition, e.g., pharmaceutical composition, comprising a therapeutically effective amount of ketamine for use in the treatment of Cluster Headache, wherein the composition is in a nasal dosage form such as a nasal spray.

14 Claims, No Drawings

(56) References Cited

OTHER PUBLICATIONS

Mitsikostas, Dimos D. et al., "Refractory chronic cluster headache: a consensus statement on clinical definition from the European Headache Federation" The Journal of Headache and Pain, 2014, pp. 1-4, vol. 15, No. 79.
Nielsen, Bettina N. et al., "Intranasal sufentanil/ketamine analgesia in children" Pediatric Anesthesia, 2014, pp. 170-180, vol. 24.
Niesters, Marieke et al., "Ketamine for chronic pain: risks and benefits" British Journal of Clinical Pharmacology, 2013, pp. 357-367, vol. 77, No. 2.
Pearson, Stuart M. et al.,"Effectiveness of Oxygen and Other Acute Treatments for Cluster Headache: Results From the Cluster Headache Questionnaire, an International Survey" Headache, 2019, pp. 235-249, vol. 59.
Schoenen, Jean et al., "Stimulation of the sphenopalatine ganglion (SPG) for cluster headache treatment. Pathway CH-1: A randomized, sham-controlled study" Cephalalgia, pp. 816-830, vol. 33, No. 10.
Shimonovich, Shachar et al., "Intranasal ketamine for acute traumatic pain in the Emergency Department: a prospective, randomized clinical trial of efficacy and safety" BMC Emergency Medicine, 2016, pp. 1-9, vol. 16, No. 43.
Sleigh, Jamie et al., "Ketamine—More mechanisms of action than just NMDA blockade" Trends in Anaesthesia and Critical Care, 2014, pp. 76-81, vol. 4.
FDA Briefing Document "Psychopharmacologic Drugs Advisory Committee (PDAC) and Drug Safety and Risk Management (DSaRM) Advisory Committee Meeting" Feb. 12, 2019, pp. 1-135.
Headache Classification Committee of the International Headache Society (IHS) "The International Classification of Headache Disorders, 3rd edition" Cephalalgia, 2018, pp. 1-211, vol. 38, No. 1.
International Search Report for PCT/IB2020/000432 dated Oct. 22, 2020.
Dias, Bruna de Freitas et al., "Current and Novel Therapies for Cluster Headache: A Narrative Review", Pain Ther. (2025), 14, pp. 1-19.
Peng, Kuan-Po et al., "Management of cluster headache: Treatments and their mechanisms", Cephalalgia, (2023) vol. 43(8), pp. 1-15.

* cited by examiner

INTRANASAL ADMINISTRATION OF KETAMINE TO CLUSTER HEADACHE PATIENTS

CROSS REFERENCE TO RELATED APPLICATIONS

This application is a U.S. National Phase Application of PCT International Application Number PCT/IB2020/000432, filed on May 29, 2020, designating the United States of America and published in the English language, which is an International Application of and claims the benefit of priority to U.S. Provisional Application No. 62/855,543, filed on May 31, 2019. The disclosures of the above-referenced applications are hereby expressly incorporated by reference in their entireties.

TECHNICAL FIELD

Disclosed is a method for treating patients with cluster headache comprising intranasal administration to a patient in need thereof of an aqueous composition, e.g., pharmaceutical composition, comprising a therapeutically effective amount of ketamine, which may reduce or eliminate side effects of ketamine when used in the treatment of Cluster headache, and to a composition, e.g., pharmaceutical composition, comprising a therapeutically effective amount of ketamine for use in the treatment of cluster headache, wherein the composition is in a nasal dosage form such as a nasal spray. In a specific embodiment, the composition is a pharmaceutical composition.

BACKGROUND ART

Cluster headache (CH), also named Horton headache, is characterized by unilateral attacks of severe pain accompanied by cranial autonomic features. Diagnostically, CH exists in two forms: an episodic (eCH) and a chronic variant (cCH), distinguished by the duration of attack free periods (Headache Classification Committee of the International Headache Society (IHS) (2018). The International Classification of Headache Disorders 3$^{rd}$ Edition. Cephalagia 38:1-211). The attacks of severe or very severe pain is orbital, supraorbital or temporal, lasting for 15 to 180 minutes and occurring from once every other day to eight times a day (Headache Classification Committee of the International Headache Society (IHS) (2018). The International Classification of Headache Disorders 3$^{rd}$ Edition. Cephalagia 38:1-211). The social impact of CH is considerable (Jensen et al. (2007) "Burden of cluster headache", Cephalalgia 27:531-41) and it is associated with sizeable direct and indirect economic consequences (Gaul et al., Treatment costs and indirect costs of cluster headache. A health economic analysis. 2011, doi:10.1177/0333105411425866). CH has a low prevalence with a 2-6 times higher average incidence rate for men compared to females (Ekbom et al. (2002) "Age at onset and sex ratio in cluster headache: observations over three decades", Cephalalgia 22:94-100). However, the ratio might be lower due to misdiagnosis of CH in women compared to men (Lund et al. (2017) "Chronobiology differs between men and women with cluster headache, clinical phenotype does not", Neurology 88: 1069-1076). The lifetime prevalence of CH based on a meta-analysis showed a mean prevalence of 124 per 100,000 with a ratio between eCH to cCH of 6 (Fischera et al. (2008) "The incidence and prevalence of cluster headache: a meta-analysis of population-based study", Cephalalgia 28:614-618). According to the Horton headache society in Denmark about 7000 patients suffers from CH in Denmark alone. The treatments to abort CH are unspecific and limited, not always effective and hampered by side effects. Some of the patients suffer from refractory CH and have no benefit of the current treatments (exact prevalence is not known). Chronic CH is defined according to a consensus statement on clinical definition from European Headache Federation (Mitsikostas et al. (2014) "Refractory chronic cluster headache: a consensus statement on clinical definition from the European Headache Federation", J. Headache and Pain 15:79). According to these guidelines, the diagnostic criteria for cCH, besides the general criteria for CH are: attacks occurring without a remission period, or with remissions lasting less than 3 months, for at least one year.

The most common drugs with known effectiveness to abort CH are triptans such as sumatriptan (subcutaneous or intranasal) or zolmitriptan (intranasal) and high-flow rate oxygen, and treatments to prevent CH are verapamil, lithium and prednisolone/dexamethasone, all dosed as tablets (Matharu (2010) "Cluster headache", Clinical Evidence 2010:02, 1212). However, not all CH patients respond to or tolerate available acute and preventive treatments, determining their CH to be refractory (Mitsikostas et al. (2014) "Refractory chronic cluster headache: a consensus statement on clinical definition from the European Headache Federation", J. Headache and Pain 15:79). These refractory patients are desperate to obtain some pain relief. A number of different drug compounds e.g. LSD with unknown effectiveness are used (are used (Matharu M. Cluster headache. Clinical Evidence, 2010:02, 1212.). A new alternative to drug treatment in CCH is neurostimulation of the sphenopalatine ganglion to relief the pain. This requires a surgery to insert a neurostimulator as mean of external self-stimulation of the nerve center by a remote controller (Schoenen et al. (2013) "Stimulation of the sphenopalatine ganglion (SPG) for cluster headache treatment. Pathway CH-1: A randomized, sham-controlled study", Cephalalgia. 33:816-30) and have shown positive results in some highly selected patients.

Ketamine (R,S-2-chlorophenyl)-2-(methylamino)-cyclohexanone), in particular the hydrochloride salt thereof, is a well-known human and veterinary anesthetic agent. Ketamine has an extremely varied set of pharmacologic actions depending on the dosage that is used. It has been in legitimate clinical use since 1963. Ketamine in its base form is highly lipophilic and easily passes the blood-brain barrier. The S-form is at least two times more potent than the R-form (Niesters et al. (2013) "Ketamine for chronic pain: risks and benefits", Br. J. Clin. Pharmacol. 2013, 77:2, 357-367). The terminal plasma half-life is 2-3 hours and the main metabolite is norketamine, which is claimed to have limited pharmacological effect (Niesters et al. (2013) "Ketamine for chronic pain: risks and benefits", Br. J. Clin. Pharmacol. 2013, 77357-367). When it is administered as an appropriate pharmacologic agent, it is a safe anesthetic agent in human and veterinary use (Sleigh et al. (2014) "Ketamine-more mechanisms of action than just NMDA blockade". Trends in anesthesia and critical care 4:76-81). The dosing for anesthetic purposes is 6.5-13.5 mg/kg of body weight. At sub-anesthetic doses (<1 mg/kg), ketamine is an uncompetitive antagonist at ionotropic NMDA-type glutamate receptors, binding to a site on the receptor while it is open. Ionotropic glutamate receptors (iGluRs) mediate the majority of excitatory neurotransmission throughout the mammalian brain. Based on their pharmacology, there are three main classes of glutamate-activated channels: α-amino-3-hydroxy-5- methyl-4-isoxazolepropionic acid receptors (AMPARs), kainate receptors, and N-methyl-d-aspartate receptors (NMDAR). Among ion-gated receptor subtypes (iGluRs), NMDAR are exceptional in their high unitary conductance, high Ca2+ permeability, and remarkably slow gating kinetics. The neuropharmacological actions of ketamine is highly complex and not fully revealed (Niesters et al. (2013) "Ketamine for chronic pain: risks and benefits", Br. J. Clin. Pharmacol 77: 357-367 and Nielsen et al. (2014) "Intranasal sufentanil/ketamine analgesia in children", Pediatric Anesthesia 24:170-180).

Intranasal administration of ketamine in sub-anesthetic dosing has been investigated in a number of clinical studies primarily in treatment of procedural pain in children (Nielsen, et al. (2014) "Intranasal sufentanil/ketamine analgesia in children", Pediatric Anesthesia 24: 170-180 and Bergmann (1999) "Ketamine: Review of its pharmacology and its use in pediatric anesthesia", Anesht. Prog. 46:10-20), in clinical practices or abortion of traumatic pain in adults (Shimonovich et al. (2016) "Intranasal ketamine for acute traumatic pain in emergency department: a prospective, randomized clinical trial of efficacy and safety", BMC Emergency Medicine, 16:43) and for treatment of major depressive disorder (Lapidus et al. (2014) "A Randomized controlled trial of intranasal ketamine in major depressive disorder", Biol. Psychiatry, 15:76970-976). In March 2019 the FDA approved a product of ketamine-S as intranasal spray for treating severe depression under clinical monitoring (NDA 211243; proprietary name SPRAVATO; esketamine hydrochloride) (FDA Briefing Document. Psychopharmacologic Drugs Advisory Committee (PDAC) and Drug Safety and Risk Management (DSaRM) Advisory Committee Meeting. Feb. 12, 2019). Ketamine nasal spray provides a rapid onset of analgesia in treatment of pediatric procedural pain management in low dose regiment (0.5 mg/kg) (Nielsen, et al. (2014) "Intranasal sufentanil/ketamine analgesia in children", Pediatric Anesthesia 24: 170-180). In two studies, the absolute bioavailability of intranasal delivery of ketamine has been estimated to 36% (Nielsen, et al. (2014) "Intranasal sufentanil/ketamine analgesia in children", Pediatric Anesthesia 24: 170-180) or 45% (Shimonovich et al. (2016) "Intranasal ketamine for acute traumatic pain in emergency department: a prospective, randomized clinical trial of efficacy and safety", BMC Emergency Medicine, 16:43). The side effects were minimal with (only slight sedation (Nielsen, et al. (2014) "Intranasal sufentanil/ketamine analgesia in children", Pediatric Anesthesia 24: 170-180). Peak plasma concentrations were obtained within 10-15 min. (Nielsen, et al. (2014) "Intranasal sufentanil/ketamine analgesia in children", Pediatric Anesthesia 24: 170-180). Ketamine nasal spray dosed 1.0 mg/kg was compared to morphine administration as IV or IM and was shown to be equal efficient in pain treatment (Shimonovich et al. (2016) "Intranasal ketamine for acute traumatic pain in emergency department: a prospective, randomized clinical trial of efficacy and safety"., BMC Emergency Medicine, 16:43). The time to onset was approx. 15 min and the side effects were mainly dizziness. No patients complained of hallucinations or out of-body experience (Shimonovich et al. (2016) "Intranasal ketamine for acute traumatic pain in emergency department: a prospective, randomized clinical trial of efficacy and safety"., BMC Emergency Medicine, 16:43). In another study, 50 mg ketamine was dosed by intranasal spray for treatment of severe depression as 5 times 100 μL over 20 minutes (Lapidus et al. (2014) "A Randomized controlled trial of intranasal ketamine in major depressive disorder", Biol. Psychiatry, 15:76970-976). No serious adverse effects occurred during the study. The treatment with nasal spray resulted in rapid improvement of the depressive symptoms and limited adverse effects (Lapidus et al. (2014) "A Randomized controlled trial of intranasal ketamine in major depressive disorder", Biol. Psychiatry, 15:76970-976).

Ketamine is categorized as a controlled drug in the U.S. and EU due to its potential recreational misuse. Ketamine can be abused in high doses and causes psychological dependence, but no physical withdrawal state is observed after cessation of long-term abuse. It can produce state of dissociated experiences out of body state and hallucinations (Sleigh, J. et al. (2014) "Ketamine-more mechanisms of action than just NMDA blockade. Trends in anesthesia and critical care" 4: 76-81). However, the risk of using ketamine in low doses for treatment of e.g. severe pain and/or major depressive conditions should be balanced by the obtained positive effects (Krusz J. C, IV ketamine in the clinic to treat Cluster Headache, poster abstract, American Academy of Neurology, published in: Supplement to Neurology:72, #11, p. A89-90, March 2009).

Intravenous treatment (IV) with ketamine has been used clinically, under very safe conditions by a very limited number of clinicians, to treat migraines, Cluster headache and other rare pain disorders including mixed headache and neuropathic pain clinical syndromes: (J. C. Krusz, IV ketamine in the clinic to treat Cluster Headache, poster abstract, American Academy of Neurology, published in: Supplement to Neurology:72, #11, p. A89-90, March 2009; Krusz, J C, Cagle, J, VB Scott-Krusz, Ketamine for treating multiple types of headaches. Poster, 14th Congress International Headache Society, in: Cephalalgia 29, Supplement 1, p. 163, October 2009; J C Krusz, J Cagle, IV Ketamine: Rapid Treatment for All TAC Subtypes in the Clinic, Abstract Poster #72, 15th Congress of the International Headache Society, Berlin, Germany, June 2011; J C Krusz, J Cagle, IM ketamine for intractable headaches and migraines, poster abstract, American Headache Society Annual Meeting, Los Angeles, Calif, June 2012; and J C Krusz, Ketamine IV—for CRPS, TN/TMD and other neuropathic pain in the outpatient clinic, poster #524, 4th International Congress on Neuropathic Pain, Toronto, Ontario, May 2013). According to J C Krusz, the drug administration by IV (usually 500-1000 mL of normal saline in a bag) is running for treatment of e.g. migraine or Cluster headache in a period of hours. Dosage is calculated on the basis of body weight and initial treatment is started at approximately 0.2-0.25 mg/kg of body weight. The dose used is far below what is administered for anesthesia (6.5-13.5 mg/kg of body weight). However, IV administration is not convenient for self-administration and can only be administered safely to patients under clinical conditions (supervision). Further, IV administration is often associated with side effects. J C Krusz has reported that patients (approximately 43% of all IV treated patients) complained of spaciness, fearfulness, jitteriness or lack of personal control. Some patients (3.2%) experienced nausea at some point during the IV treatment. US 2014/0275278 discloses use of ketamine (S-ketamine) nasal spray for self-administering treatment of severe depression. US 1996/5543434 discloses (R,S)-ketamine for treatment of general pain.

Accordingly, there is a continuing need for providing a dosage form of ketamine in an amount effective for the treatment of patients suffering from Cluster headache with fewer or no side effects than the known treatments, and for providing a dosage form useful for safe self-administration for the convenience of the patients.

SUMMARY

It has surprisingly and unexpectedly been found that patients suffering from Cluster headache (CH), either chronic CH (cCH) or episodic CH (eCH), advantageously may be treated with intranasal ketamine, that is by nasal systemic drug delivery of a composition, comprising ketamine. The composition in a specific embodiment may be a pharmaceutical composition. Surprisingly, the use of this dosage form for treatment of CH patients with the active pharmaceutical ingredient ketamine in doses essentially corresponding to the doses used in intravenous (IV) administration results in patient relief while eliminating or significant reducing undesirable side effects of ketamine such as for example nausea, dysphoria and spaciness.

Also, intranasal delivery of ketamine provides the option of safe self-administration of the active pharmaceutical ingredient to CH patients in need thereof.

In a particular embodiment, the composition, e.g., pharmaceutical composition, comprising ketamine is administered intranasally in an amount resulting in a systemic absorbed dose essentially corresponding to or lower than the absorbed dose resulting from intravenous (IV) administration, whereby, the side effects of ketamine are reduced or eliminated.

Another embodiment is a method of treating patients with cluster headache comprising intranasal administration to a patient in need thereof of an aqueous composition, e.g., pharmaceutical composition, comprising a therapeutically effective amount of ketamine, an amount effect to treat said cluster headache.

Yet another embodiment is a composition, e.g., pharmaceutical composition, comprising a therapeutically effective amount of ketamine for use in the treatment of cluster headache, wherein the composition is in a nasal dosage form.

In any of the embodiments, the intranasal administration may be in the form of nasal spray or nasal drops. The nasal spray may be a one-use device containing a single dose or up to 10 doses, preferably not more than 5 doses.

In any of the embodiments, the active pharmaceutical ingredient ketamine is preferably selected from the group consisting of the hydrochloride salts of (R,S)-ketamine and S-ketamine.

In any of the embodiments, the therapeutically effective amount of ketamine may be at least about 5 mg, or at least about 10 mg, or at least about 15 mg of ketamine base (2-(2-chlorophenyl)-2-(methylamino)cyclohexanone), delivered in a single dose or unit dose, based on the therapeutic effect of S-ketamine. In a further embodiment, the therapeutically effective amount of ketamine is not higher than about 150 mg, or not higher than about 100 mg, or not higher than about 75 mg, or not higher than about 50 mg of ketamine base (2-(2-chlorophenyl)-2-(methylamino) cyclohexanone), delivered in a single dose or unit dose, based on the therapeutic effect of S-ketamine.

The patient in any of the embodiments described above may suffer from Cluster headache (CH), either chronic CH or episodic CH.

DETAILED DESCRIPTION OF THE DISCLOSURE

Where a range of values are provided, it is understood that each intervening value, to the tenth of the unit of the lower limit unless the context clearly dictates otherwise, between the upper and lower limit of that range and any other stated or intervening value in that stated range is encompassed. The upper and lower limits of these smaller ranges may independently be included in the smaller ranges is also encompassed, subject to any specifically excluded limit in the stated range. Where the stated range includes one or both of the limits, ranges excluding either both of those included limits are also included.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this disclosure are incorporated by reference in their entirety. Nothing herein is to be construed as an admission that the subject matter disclosed and claimed in the instant application is not entitled to antedate such disclosure by virtue of prior invention. To the extent the material incorporated by reference contradicts or is inconsistent with this specification, the specification will supersede any such material.

It must be noted that as used herein and in the appended claims, the singular forms "a," "and" and "the" include plural references unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. Thus, the terms "comprising", "including," containing", "having" etc. shall be read expansively or open-ended and without limitation.

As used herein, the term "composition" is intended to encompass a product comprising the specified ingredients in the specified amounts, as well as any product which results, directly or indirectly, from combinations of the specified ingredients in the specified amounts. A composition also includes a "pharmaceutical composition", defined infra.

As used herein, unless otherwise noted, the terms "S-ketamine" and "S ketamine hydrochloride" shall mean the (S)-enantiomer of ketamine, as its corresponding hydrochloride salt, a compound known as (S)-2-(2-chlorophenyl)-2-(methylamino)cyclohexanone hydrochloride.

As used herein, unless otherwise noted, the term "ketamine" (2-(2-chlorophenyl)-2-(methylamino)cyclohexanone) shall mean any of R,S-ketamine, R,S-ketamine hydrochloride, S-ketamine, S-ketamine hydrochloride, R-ketamine, R-ketamine hydrochloride. As used herein, the amount of ketamine present in the composition, e.g., pharmaceutical composition, used according to the invention refers to the weight/molecular weight of the ketamine base (2-(2-chlorophenyl)-2-(methylamino)cyclohexanone). The weight/molecular weight ratio of the hydrochloride salt of ketamine to that of the ketamine base is 1.15.

The term "pharmaceutical composition" includes any pharmaceutical preparation or formulation that is customized for being administered to a human being or animal.

Preferably, the composition contains one or more physiologically acceptable carriers and/or excipients. Preferably, the pharmaceutical compositions used herein contain water.

As used herein, unless otherwise noted, the term "aqueous" shall mean that the primary liquid component of the formulation is water. Preferably, water constitutes greater than about 80 wt % of the liquid component of the composition, e.g., pharmaceutical composition, more preferably greater than about 90 wt %, more preferably greater than about 95 wt %, more preferably about 98 wt %.

The hydrochloride salt of ketamine is water-soluble and has a pKa of 7.5. It has a chiral center at C-2 carbon of the cyclohexanone ring. Accordingly, two enantiomers exist: S-(+)-ketamine and R-(−)-ketamine. The pharmacological activity of the S-(+) enantiomer is up to three times higher than of the R-(−) enantiomer. Ketamine is a white or almost white crystalline powder. Ketamine is freely soluble in water (1:4) and in methyl alcohol; soluble in alcohol (USP). A 10% aqueous solution has a pH of between 3.5 and 4.1.

To prepare the composition, e.g., pharmaceutical composition, disclosed herein, ketamine hydrochloride as the active ingredient is intimately admixed with a pharmaceutical carrier, preferably water, according to conventional pharmaceutical compounding techniques, which carrier may take a wide variety of forms depending on the form of preparation desired for administration. Suitable pharmaceutically acceptable carriers are well known in the art. Descriptions of these pharmaceutically acceptable carriers may be found in The Handbook of Pharmaceutical Excipients, published by the American Pharmaceutical Association and the Pharmaceutical Society of Great Britain.

Methods of formulating the compositions, including pharmaceutical compositions, set forth below have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dos-age Forms: Disperse Systems, Volumes 1-2, edited by Lieberman et al; published by Marcel Dekker.

Preferably, the composition, e.g., pharmaceutical composition, used is an aqueous formulation comprising water and ketamine, wherein ketamine is present in an amount in the range of from about 50 mg/mL to about 200 mg/mL, or any amount or range therein, based on the total volume of the composition, e.g., pharmaceutical composition. Preferably, ketamine is present in an amount in the range of from about 50 mg/mL to about 150 mg/mL, or any amount or range therein. More preferably, ketamine is present in an amount in the range of from about 150 mg/mL to about 175 mg/mL, or any amount or range therein. Even more preferably, ketamine is present in an amount in the range of from about eq. 100 mg/mL to about eq. 200 mg/mL, or any amount or range therein, based on the total volume of said composition.

The composition, e.g., pharmaceutical composition, used accordingly may comprise one or more buffers and/or buffer systems (i.e. conjugate acid/base pairs). As used herein, the term "buffer" shall mean any solid or liquid composition (preferably an aqueous, liquid composition) which, when added to an aqueous formulation, adjusts the pH of said formulation. The skilled person will recognize that a buffer may adjust the pH of the aqueous formulation in any direction (toward more acidic, more basic or more neutral pH). Preferably, the buffer is pharmaceutically acceptable.

Suitable examples of buffers which may be used in the compositions disclosed herein include, but are not limited to: citric acid, sodium dihydrogen phosphate, disodium hydrogen phosphate, sodium hydroxide, acetic acid, boric acid, sodium borate, succinic acid, tartaric acid, malic acid, lactic acid, fumaric acid, and the like. Preferably, the buffer or buffer system is selected from the group consisting of sodium hydroxide, citric acid, sodium dihydrogen phosphate and disodium hydrogen phosphate.

The buffer is selected to adjust the pH of the compositions, e.g., pharmaceutical compositions, used (e.g. the aqueous formulations described herein) into a pH in the range of from about pH 3.5 to about pH 6.5 or any amount or range therein, preferably from about pH 4.0 to about pH 5.5 or any amount or range therein, more preferably from about pH 4.5 to about pH 5.0 or any amount or range therein. Preferably, the concentration of the buffer and buffer system, respectively, preferably sodium hydroxide (NaOH), is adjusted to provide a sufficient buffer capacity.

In a preferred embodiment, the composition, e.g., pharmaceutical composition, used comprises ketamine hydrochloride, water, and a buffer or buffer system, preferably NaOH, wherein the buffer or buffer system is present in an amount sufficient to provide a pH in the composition in the range of from about pH 4.0 to about pH 6.0, or any amount or range therein.

The composition, e.g., pharmaceutical composition, used may comprise a preserving agent or preservative.

As used herein, unless otherwise noted, the terms "antimicrobial preservative" and "preservative" shall mean any substance conventionally used in compositions, e.g., pharmaceutical compositions, in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

Preferably, the composition, e.g., pharmaceutical composition, used is free of preservatives, when the content of ketamine hydrochloride present in the composition is adequate for achieving the desired shelf life or in use stability due to the preservative property of the API as such. As used herein, the terms "penetration agent", "penetration enhancer", and "penetrant" refer to any substance that increases or facilitates absorption and/or bioavailability of the active ingredient ketamine hydrochloride. Preferably, a useful penetration agent increases or facilitates absorption and/or bioavailability of ketamine through the mucous membrane after nasal administration.

Suitable penetrating agents include, but are not limited to, tetradecyl maltoside, sodium glycocholate, lecithin, chitosan and salts thereof, and surface active ingredients such as benzalkonium chloride, sodium dodecyl sulfate and sodium docusate.

The intranasal administration of the composition, e.g., pharmaceutical composition, used according to the invention is carried out by administering nose drops comprising the composition or by nasal spray comprising the composition. The nasal spray is preferably a one-dose container type comprising up to about 50 mg or about 75 mg of S-ketamine, preferably as the hydrochloride salt. The nasal spray is manually activated and typically dosing about 5-10 mg of S-ketamine per spray in the nostril, typically corresponding to about 50-100 μL of the composition, e.g., pharmaceutical composition, disclosed herein. The patient is administering one spray in a nostril repeatedly at certain time intervals, for example 6 minutes, until headache relief is obtained.

The composition, e.g., pharmaceutical composition, used according to the invention in a nasal spray or as nose drops may contain a local anesthetic, e.g. lidocaine, in order to suppress local pain or discomfort due to the delivery of ketamine in the nose.

EXAMPLES

The following examples serve the purpose of illustrating the invention and are not intended to limiting the scope of the present invention.

Example 1—Open Pilot Study

The objective of the open pilot study was to evaluate whether ketamine administered as an intranasal spray in sub-anesthetic doses is effective in treatment of chronic Cluster Headache (cCH).

Method—Study Design: The study was conducted at the Danish Headache Center, Rigshospitalet-Glostrup (Copenhagen University Hospital, Denmark) from October 2019 to April 2020. The cCH patients were dosed with an intranasal spray containing 172.5 mg ketamine hydrochloride (corresponding to 150 mg ketamine base) per ml in an aqueous solution. The individual dosing included 15 mg ketamine as ketamine hydrochloride salt in an intranasal sprayed volume of 100 μL given in one nose nostril under supervision of a nurse.

The treatment was initiated at T=0 (T0) under a CH attack when the headache pain exceeds NRS=6 on an NRS pain scale. The first intranasal dose of 15 mg was given at T=0 and at time intervals of 6 minutes. At 15 minutes after 3 doses (45 mg) it was evaluated whether the patient was sufficiently pain relieved (e.g. NRS<4) or wanted to receive rescue medications instead or, if pain was not sufficiently relieved, wanted to continue until 5 doses (75 mg) were received at time point T=24. The final evaluation of the treatment was performed at T=30. During the study the primary response was the NRS score. Associated parameters such as blood pressure, heart rate and oxygen saturation were monitored as well as potential adverse effects. The NRS scale refers to Numeric Rating Scale of pain (0=no pain; 1-3=mild pain; 4-6=moderate pain; 7-9=severe pain; 10=worst pain imaginable).

Pharmacokinetic Modeling and Intranasal Dosing

The PK-model of ketamine follows a two-compartment model (central volume (plasma) compartment and peripheral compartments).

Ketamine was absorbed in this case from the intranasal cavity into the central volume (plasma) where it distributes and redistributes to deeper peripheral compartments. The elimination follows oxidation primarily via the CYP3A4 enzyme system in the liver to norketamine and further into other metabolites, all of which are pharmacologically inactive. The rate constants were taken from BMC Emergency Medicine, 2016, 16:43 including estimation of the first order absorption rate constant from the intranasal reservoir. The following first order rate constants were applied to the model as $k_a$=5.73 $h^{-1}$, $k_{12}$=8.84 $h^{-1}$, $k_{21}$=1.62 $h^{-1}$ and $k_{10}$=1.55 $h^{-1}$. The terminal elimination half-life was approx. 2 hours (β-phase). The resulting plasma profile derived from numerical cumulation in the simulation program Stella® 8.0 by input of 6 consecutive intranasal dosing of 15 mg with time interval of 6 minutes results in the plasma profile shown according to study design. It was assumed that the person has a body weight of 70 kg and a central distribution volume of 24 L. The concentration in plasma of ketamine on the y-axis was given as mg in the central distribution volume. A total of 15 mg ketamine was dosed 5 times corresponding to 75 mg. The bioavailability was approx. 50%. It means a maximum exposure of a 0.5 mg/kg of body weight which was significantly below the dosing for anesthesia (min 6.5 mg/kg of body weight).

Statistical Analysis

Formal calculation of required study size requires knowledge of standard deviation in response (NRS score) for treatment of CCH with intranasal ketamine. Since these data are not available the sample size was determined based on what was normally seen in similar POC pilot studies, which is n=20. The mean pain intensity at peak (NRS-score) and pain at T15 and T30 (NRS-score) is compared using the paired t-test.

Experimental Procedures, Patients

The patients enrolled for the trial complied with the diagnostic criteria of chronic CH as defined in the International Classification of Headache Disorders 3' Edition. Patient inclusion criteria were: signed informed consent; age 18-60 years; body weight at least 50 kg and BMI not higher than 30; diagnosed with cCH according to ICHD-3 criteria. Patient exclusion criteria were: Conditions that result in the patient being unable to complete the experiment; medical history with elevated intraocular pressure (e.g. glaucoma); medical history of elevated intraocular pressure (e.g. glaucoma); medical history of severe heart or liver disease; aneurysmal vascular disease or arteriovenous malformations; medical history with severe neurological disease except of headache; blood pressure measured at baseline before CH attack (systolic>140 mmHg or/and diastolic blood pressure>90 mmHg); medical history with severe depression or psychosis; a previous history of drug abuse; consumption of illegal drugs within the last 6 months; medical history of nasal abnormality or dysfunction (e.g. rhinitis); high disposition for larynges or apnea; positive pregnancy test before treatment and breastfeeding; known hypersensitivity to ketamine.

If the patient met all criteria for participation in the one-day in-hospital observation, a stay iwa scheduled. If the patient approved for the clinical study had no CH attack during the one-day hospitalization, the patient was invited to a second appointment.

The study drug was administered to the patient (trial participant) during a one-day in-hospital observational stay at the department of neurology N38 at Rigshospitalet-Glostrup. The ward is a highly specialized ward only admitting patients with headache disorders for focused stays of either diagnostic or treatment intent. All nurses affiliated with the ward are specially trained in caring for and treating headache patients. Trial participants were admitted to the ward in order to observe the patients for CH attacks and administration of study drug if an attack does develop. If the participant developed a CH attack, he/she contacted the nurse on call for administration of study drug. During the CH attack, the patient was dosed under supervision of a nurse, and the effect and eventually side effects were observed according to the study design. One to two weeks after the trial, the patient was interviewed by telephone for feedback on positive effect or negative effect and adverse effects, if any.

The primary end-point of the study: A 50% or more reduction in pain on a ten-point NRS scale (0: no pain, 10: worst imaginable pain) at T=15 from pain intensity at T=0 (T0).

The secondary endpoints are: A 50% or more reduction in pain on a ten-point NRS scale (0: no pain, 10: worst imaginable pain) at T=30 from pain intensity at T=0; a 25% reduction in pain on a ten-point NRS scale (0: no pain, 10: worst imaginable in) at T15 from pain intensity at T=0; proportion of patients reporting less than 4 (NRS scale) at T=15; proportion of patients reporting less than 4 (NRS scale) at T=30; proportion of patients receiving rescue medication at T=15; proportion of patients preferring ketamine treatment compared to oxygen or injectable sumatriptan; proportion of patients experiencing serious side effects during treatment.

Study results. A total of 23 patients (n=23) were enrolled in the study (from 58 patients assessed for eligibility): the study drug (ketamine nasal spray) was administered to 20 patients (n=20), 3 patients (n=3) did not receive the study drug, cf. Table 1.

TABLE 1

| Patient population | | | |
|---|---|---|---|
| | n = 20 | n = 3 | Overall (n = 23) |
| Age (yrs) | 47 (27-59) | 48 (30-60) | 47 (27-60) |
| Sex - no. of males | 15 (75%) | 1 (33%) | 16 (70%) |
| Sex - no. of females | 5 (25%) | 2 (67%) | 7 (30%) |
| CH duration (yrs) | 20.2 (4-49) | 15.0 (7-23) | 19.5 (4-49) |
| Attack duration (min) | 88 (30-180) | 150 (120-180) | 96.1 (30-180) |
| Refractory | 0.45 (0-1) | 0.67 (0-1) | 0.48 (0-1) |

Refractory: Patients not responding to any prophylactic treatment, cf. definition from the European Headache Federation.

Data (values) shown in Table 1 are mean (min–max)

Primary end-point (at least 50% reduction in pain on a ten-point NRS scale at T=15 min) results:

Negative (15%)

T=0 (mean, SD): 7.15 (1.24)

T=15 (mean, SD); 6.1 (3.06)

p-value: 0.188

Secondary end-point results (Table 2):

TABLE 2

| Results secondary end-points | |
|---|---|
| At least 50% reduction in pain on a ten-point NRS scale at T = 30 min | Positive (59% reduction)<br>T = 0 (mean, SD): 7.25 (1.24)<br>T = 30 (mean, SD): 2.94 (3.40)<br>p-value: 0.0002 |
| At least 25% reduction in pain on a ten-point NRS scale at T = 15 min | Negative (15%)<br>T = 0 (mean, SD): 7.15 (1.27)<br>T = 15 (mean, SD): 6.1 (3.06) |
| Proportion of patients reporting less than 4 (NRS scale) at T = 15 min | 3/20 |
| Proportion of patients reporting less than 4 (NRS scale) at T = 30 min | 11/16 |
| Proportion of patients receiving rescue medication at T = 15 min | 4/20 |
| Proportion of patients preferring ketamine treatment compared to oxygen or injectable sumatriptan | 10/20 |
| Serious adverse effects | 0/20 |

The study results show a significant reduction of pain in chronic CH patients 30 minutes after the first administration of the ketamine nasal spray study drug according to the study protocol without any serious adverse effects. Accordingly, cCH patients may have the option of using ketamine nasal spray for pain relief as an alternative to known treatments.

Example 2—Case Studies (1-3)

Individual Cluster headache patients were treated with sub-anesthetic doses of intranasal ketamine (conventional manual nasal spray device administering 100 μL to one nose nostril of a composition of 50-150 mg ketamine as ketamine hydrochloride dissolved in an aqueous solution of 0.9% sodium chloride).

Case 1: A 38 years old male, with cluster headaches for about 16 years and with a family history of the same, had been tried on a number of acute and prophylaxis agents in his treatment of the cluster with at best a shortening of the cluster headache episode. The cluster headaches tended to flare up in the springtime lasting up to three months at a time with about 4 to 6 episodes per day. This prevented him from working. In the outpatient clinic he received IV treatment with ketamine, which resulted in the complete cessation of the cluster headaches in three days of dedicated IV treatment (with resolution of allodynia on the right side as well). He was very pleased and elected to try intranasal ketamine at the first onset of the next cluster headache episode. 15 mg per nasal spray were used, as described above. He had no side effects to the ketamine (like dysphoria or out-of-body side effects). He reported feeling better after 2-3 sprays and feeling calm as well. Sometimes, he had to repeat the dosing in the AM or the next day.

Case 2: A 55 years old woman had cluster headaches episodically, along with three to four per week migraines, along with chronic neck pain and trigeminal neuralgia (TN) on the right side. The cluster headaches started at age 27, with tearing, allodynia and facial numbness. Sometimes the migraine would evolve into a cluster episode that came on during her sleep and was seasonal as well, lasting about 2 months on average. She was not a smoker and there was no family history of cluster headache. There was a family history of migraines, though. She was treated very successfully for the migraines, right TN and neck pain with Botox treatments, every 3-5 months, supplemented by other prophylaxis neuropathically-active medications, but no opiates. The Botox treatment did not affect the cluster headaches, except where they evolved from the migraines, and only to a slight extent [15-20%]. Multiple acute and prophylaxis therapies were attempted to resolve the cluster headache episodes to no significant avail. IV ketamine was tried on one occasion in a four day series of treatments during a cluster headache episode and shut off the ongoing process from 5 episodes per day to only one cluster headache in the next week and resolving with extra oral oxcarbazepine dosage of 600 mg. Nasal spray ketamine was then compounded at 10 mg per 0.1 cc spray with the suggestion that she spray one nostril, the right one, every 10-15 minutes to give the medical time to absorb from the nasal mucosa and to repeat the process until at least 75% relief was obtained. She was very happy with this approach as it gave her control of her hardest to treat symptom. She also noticed that the cluster headache episodes were beginning to get less frequent over about a year and her migraines and TN also definitely got better and Botox intervals were longer over time.

Case 3: A 34 years old male, who worked in the construction industry began having episodic cluster headache episodes at age 22. There was a migraine and cluster headache history in the family as well. The cluster headache was season-specific, occurring mostly in the early summer of each or every other year. They were very disabling and often awoke this gentleman from a sound sleep for several weeks. He had been given many oral medications, including opiates, for suppression of his symptoms without any real benefit and many side effects. When visiting the outpatient clinic, he was treated with IV lidocaine, IV Depacon and IV Magnesium sulfate with only partial success in shutting the episode down. He was offered IV treatment with ketamine during the beginning of one of his episodes, and it proved to work more effectively and to shorten the duration of the cluster episode by greater than two-thirds [6-7 weeks to one week-10 days]. On this result, he received compounded nasal spray ketamine [7.5 mg per 0.1 cc spray], and was instructed to use this at bedtime, with additional sprays in one nostril, the affected side of the cluster headache, every 10 minutes until significant relief was obtained to at least 75%. He was also instructed to use the same approach during the day when the cluster headache returned. He used nasal spray ketamine for several years and his overall pattern became easier to treat successfully. The episodes grew further apart and he has only had one short cluster headache episode in the last three to four years.

For the cases 1-3: On a 0 to 10 Visual Analogue Scale (VAS) patients were above 65% from initial baseline from the use of the ketamine spray. The Visual Analogue Scale (VAS) consists of a straight line with the endpoints defining extreme limits such as 'no pain at all' and 'pain as bad as it could be'. The patient was asked to mark his pain level on the line between the two endpoints. The distance between 'no pain at all' and the mark then defines the subject's pain. Efficacy, as well as safety and tolerability, of sub-anesthetic low dose IV ketamine were seen consistently. Increased dysphoria or nausea was not noted. No out-off body experiences, or hallucinations were observed.

In conclusion, intranasal ketamine is a legitimate pharmacologic treatment and is safe and effective for cluster headache rescue. It adds another new dimension to treatment of out-of-control cluster headaches in an outpatient setting with no monitoring. Intranasal ketamine represents an extremely viable and specific pharmacologic agent with a very specific mechanism of action on blockade of NMDA-type and perhaps other subtypes of the same glutamate receptor family and truly represents a new treatment option.

What is claimed is:

1. A method of treating a patient suffering from chronic cluster headache comprising intranasally self-administering to said patient an aqueous solution comprising dissolved ketamine in a range from 50 mg/mL to 200 mg/mL based on the total volume of the aqueous solution, wherein the dissolved ketamine is administered in an amount corresponding to 15 mg ketamine in each dose using a nasal spray having a one-dose container comprising 15 mg ketamine, wherein the intranasal administration of the aqueous solution comprises administration of a total of from 3 doses containing 15 mg ketamine in each dose using one dose containers (45 mg total) to 5 doses containing 15 mg ketamine in each dose using one-dose containers (75 mg total), wherein doses are administered at time intervals of 6-15 minutes, wherein ketamine is administered as the only active pharmaceutical ingredient for the treatment of chronic cluster headache, and wherein the intranasal administration is performed upon onset of a cluster headache episode.

2. The method according to claim 1, wherein the ketamine is (R,S)-ketamine hydrochloride.

3. The method according to claim 1, wherein the ketamine is S-ketamine hydrochloride.

4. The method according to claim 1, wherein the composition comprising ketamine is administered in an amount resulting in a systemic absorbed dose corresponding to or lower than the absorbed dose resulting from intravenous (IV) administration, whereby side effects of ketamine when used in the treatment of chronic cluster headache are reduced or eliminated compared to IV administration of said amount.

5. The method according to claim 1, wherein the ketamine is administered as ketamine base (2-(2-chlorophenyl)-2-(methylamino) cyclohexanone).

6. The method according to claim 1, wherein the aqueous solution has a pH in a range of from 4.0 to 6.5.

7. The method according to claim 1, wherein a total of 3 doses are administered.

8. The method according to claim 1, wherein the aqueous solution comprises dissolved ketamine in a range of from 100 mg/mL to 200 mg/ml based on the total volume of the aqueous solution.

9. The method according to claim 1, wherein each dose has a total volume of 100 μL aqueous solution.

10. The method according to claim 1, wherein the treatment is for out-of-control chronic cluster headaches.

11. The method according to claim 1, wherein the treatment eliminates or reduces undesirable side effects.

12. The method according to claim 1, wherein the treatment eliminates or reduces side effects selected from the group consisting of nausea, dysphoria and spaciness.

13. The method according to claim 1, wherein said aqueous solution consists essentially of ketamine and one or more pharmaceutically acceptable carriers or excipients.

14. The method according to claim 1, wherein the treatment is for chronic cluster headaches where other treatments have failed.

* * * * *